US007651462B2

(12) United States Patent
Hjelle et al.

(10) Patent No.: US 7,651,462 B2
(45) Date of Patent: Jan. 26, 2010

(54) CARDIAC SUPPORT DEVICE DELIVERY TOOL WITH RELEASE MECHANISM

(75) Inventors: Aaron J. Hjelle, Champlin, MN (US); James Edward Shapland, Vadnais Heights, MN (US); Michael Andreini, Stillwater, MN (US); Dan Titcomb, St. Paul, MN (US); Jeffrey Popowski, Roseville, MN (US); Bradley Knippel, Lino Lakes, MN (US)

(73) Assignee: Acorn Cardiovascular, Inc., St. Paul, MN (US)

( * ) Notice: Subject to any disclaimer, the term of this patent is extended or adjusted under 35 U.S.C. 154(b) by 267 days.

(21) Appl. No.: 11/487,953

(22) Filed: Jul. 17, 2006

(65) Prior Publication Data

US 2008/0033234 A1 Feb. 7, 2008

(51) Int. Cl.
*A61F 2/00* (2006.01)
(52) U.S. Cl. ........................................ 600/37
(58) Field of Classification Search .................. 600/16, 600/17, 37; 606/139, 185, 195, 202
See application file for complete search history.

(56) References Cited

U.S. PATENT DOCUMENTS

| 1,682,119 | A | 8/1928 | Field |
| 1,965,542 | A | 7/1934 | Colvin Jr. |
| 1,982,207 | A | 11/1934 | Furniss |
| 2,138,603 | A | 11/1938 | Johnson |
| 2,278,926 | A | 4/1942 | Hartwell |
| 2,376,442 | A | 5/1945 | Mehler |
| 2,992,550 | A | 7/1961 | Frith |
| 3,384,530 | A | 5/1968 | Mercer et al. |
| 3,452,742 | A | 7/1969 | Muller |
| 3,551,543 | A | 12/1970 | Mercer et al. |
| 3,587,567 | A | 6/1971 | Schiff |
| 3,732,662 | A | 5/1973 | Paxton |
| 3,768,643 | A | 10/1973 | Bruno |
| 3,983,863 | A | 10/1976 | Janke et al. |
| 4,048,990 | A | 9/1977 | Goetz |

(Continued)

FOREIGN PATENT DOCUMENTS

DE          3 24 524          8/1920

(Continued)

OTHER PUBLICATIONS

"Abstracts From the 68th Scientific Sessions, Anaheim Convention Center, Anaheim, California, Nov. 13-16, 1995", *American Heart Association Supplement to Circulation*, vol. 92, No. 8, Abstracts 1810-1813 (Oct. 15, 1995).

(Continued)

*Primary Examiner*—Charles A Marmor, II
*Assistant Examiner*—Christine D Hopkins
(74) *Attorney, Agent, or Firm*—Faegre & Benson LLP

(57) ABSTRACT

An apparatus for placing a cardiac support device (CSD) on a heart. The apparatus includes a body, a deployment mechanism on the body for supporting the CSD in an open position for placement on the heart, and a release mechanism coupled to the deployment mechanism for releasably mounting the CSD to the deployment mechanism. The release mechanism includes a release element for releasably engaging the CSD, and a release actuator coupled to the release element for actuating the release element to release the CSD.

19 Claims, 17 Drawing Sheets

U.S. PATENT DOCUMENTS

| | | |
|---|---|---|
| 4,196,534 A | 4/1980 | Shibamoto |
| 4,403,604 A | 9/1983 | Wilkinson et al. |
| 4,428,375 A | 1/1984 | Ellman |
| 4,466,331 A | 8/1984 | Matheson |
| 4,536,893 A | 8/1985 | Parravicini |
| 4,567,900 A | 2/1986 | Moore |
| 4,598,039 A | 7/1986 | Fischer et al. |
| 4,630,597 A | 12/1986 | Kantrowitz et al. |
| 4,637,377 A | 1/1987 | Loop |
| 4,690,134 A | 9/1987 | Snyders |
| 4,790,850 A | 12/1988 | Dunn et al. |
| 4,821,723 A | 4/1989 | Baker, Jr. et al. |
| 4,827,932 A | 5/1989 | Ideker et al. |
| 4,834,707 A | 5/1989 | Evans |
| 4,840,626 A | 6/1989 | Linsky et al. |
| 4,878,890 A | 11/1989 | Bilweis |
| 4,932,972 A | 6/1990 | Dunn et al. |
| 4,936,857 A | 6/1990 | Kulik |
| 4,957,477 A | 9/1990 | Lundback |
| 4,973,300 A | 11/1990 | Wright |
| 4,976,730 A | 12/1990 | Kwan-Gett |
| 4,995,857 A | 2/1991 | Arnold |
| 5,042,463 A | 8/1991 | Lekholm |
| 5,057,117 A | 10/1991 | Atweh |
| 5,074,129 A | 12/1991 | Matthew |
| 5,087,243 A | 2/1992 | Avitall |
| 5,131,905 A | 7/1992 | Grooters |
| 5,150,706 A | 9/1992 | Cox et al. |
| 5,186,711 A | 2/1993 | Epstein |
| 5,188,813 A | 2/1993 | Fairey et al. |
| 5,192,314 A | 3/1993 | Daskalakis |
| 5,207,725 A | 5/1993 | Pinkerton |
| 5,224,363 A | 7/1993 | Sutton |
| 5,256,132 A | 10/1993 | Snyders |
| 5,279,539 A | 1/1994 | Bohan et al. |
| 5,290,217 A | 3/1994 | Campos |
| 5,336,253 A | 8/1994 | Gordon et al. |
| 5,339,657 A | 8/1994 | McMurray |
| 5,341,815 A | 8/1994 | Cofone et al. |
| 5,356,432 A | 10/1994 | Rutkow et al. |
| 5,366,460 A | 11/1994 | Eberbach |
| 5,383,840 A | 1/1995 | Heilman et al. |
| 5,385,156 A | 1/1995 | Oliva |
| 5,405,360 A | 4/1995 | Tovey |
| 5,409,703 A | 4/1995 | McAnalley et al. |
| 5,429,584 A | 7/1995 | Chiu |
| 5,507,779 A | 4/1996 | Altman |
| 5,524,633 A | 6/1996 | Heaven et al. |
| 5,533,958 A | 7/1996 | Wilk |
| 5,558,617 A | 9/1996 | Heilman et al. |
| 5,593,441 A | 1/1997 | Lichtenstein et al. |
| 5,603,337 A | 2/1997 | Jarvik |
| 5,611,515 A | 3/1997 | Benderev et al. |
| 5,647,380 A | 7/1997 | Campbell et al. |
| 5,695,525 A | 12/1997 | Mulhauser et al. |
| 5,702,343 A | 12/1997 | Alferness |
| 5,713,954 A | 2/1998 | Rosenberg et al. |
| 5,735,290 A | 4/1998 | Sterman et al. |
| 5,766,216 A | 6/1998 | Gangal et al. |
| 5,782,746 A | 7/1998 | Wright |
| 5,800,334 A | 9/1998 | Wilk |
| 5,800,528 A | 9/1998 | Lederman et al. |
| 5,839,842 A | 11/1998 | Wanat et al. |
| 5,853,422 A | 12/1998 | Huebsch et al. |
| 5,928,250 A | 7/1999 | Koike et al. |
| 5,931,810 A | 8/1999 | Grabek |
| 5,961,440 A | 10/1999 | Schweich, Jr. et al. |
| 5,972,013 A | 10/1999 | Schmidt |
| 5,990,378 A | 11/1999 | Ellis |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,076,013 A | 6/2000 | Brennan et al. |
| 6,077,214 A | 6/2000 | Mortier et al. |
| 6,077,218 A | 6/2000 | Alferness |
| 6,085,754 A | 7/2000 | Alferness et al. |
| 6,089,051 A | 7/2000 | Gorywoda et al. |
| 6,095,968 A | 8/2000 | Snyders |
| 6,123,662 A | 9/2000 | Alferness et al. |
| 6,126,590 A | 10/2000 | Alferness |
| 6,155,968 A | 12/2000 | Wilk |
| 6,155,972 A | 12/2000 | Nauertz et al. |
| 6,165,121 A | 12/2000 | Alferness |
| 6,165,122 A | 12/2000 | Alferness |
| 6,169,922 B1 | 1/2001 | Alferness et al. |
| 6,174,279 B1 | 1/2001 | Girard |
| 6,179,791 B1 | 1/2001 | Krueger |
| 6,193,648 B1 | 2/2001 | Krueger |
| 6,205,747 B1 | 3/2001 | Paniagua Olaechea |
| 6,206,004 B1 | 3/2001 | Schmidt et al. |
| 6,224,540 B1 | 5/2001 | Lederman et al. |
| 6,230,714 B1 | 5/2001 | Alferness et al. |
| 6,241,654 B1 | 6/2001 | Alferness |
| 6,293,906 B1 | 9/2001 | Vanden Hoek et al. |
| 6,360,749 B1 | 3/2002 | Jayaraman |
| 6,370,429 B1 | 4/2002 | Alferness et al. |
| 6,375,608 B1 | 4/2002 | Alferness |
| 6,402,680 B2 | 6/2002 | Mortier et al. |
| 6,416,459 B1 | 7/2002 | Haindl |
| 6,425,856 B1 | 7/2002 | Shapland et al. |
| 6,432,039 B1 | 8/2002 | Wardle |
| 6,482,146 B1 | 11/2002 | Alferness et al. |
| 6,508,756 B1 | 1/2003 | Kung et al. |
| 6,517,570 B1 | 2/2003 | Lau et al. |
| 6,537,203 B1 | 3/2003 | Alferness et al. |
| 6,541,678 B2 | 4/2003 | Klein |
| 6,544,168 B2 | 4/2003 | Alferness |
| 6,564,094 B2 | 5/2003 | Alferness et al. |
| 6,567,699 B2 | 5/2003 | Alferness et al. |
| 6,569,082 B1 | 5/2003 | Chin |
| 6,572,533 B1 | 6/2003 | Shapland et al. |
| 6,579,226 B2 | 6/2003 | Vanden Hoek et al. |
| 6,582,355 B2 | 6/2003 | Alferness et al. |
| 6,587,734 B2 | 7/2003 | Okuzumi |
| 6,602,184 B2 | 8/2003 | Lau et al. |
| 6,612,978 B2 | 9/2003 | Lau et al. |
| 6,612,979 B2 | 9/2003 | Lau et al. |
| 6,620,095 B2 * | 9/2003 | Taheri .................. 600/37 |
| 6,645,139 B2 | 11/2003 | Haindl |
| 6,663,558 B2 | 12/2003 | Lau et al. |
| 6,673,009 B1 | 1/2004 | Vanden Hoek et al. |
| 6,682,474 B2 | 1/2004 | Lau et al. |
| 6,682,475 B2 | 1/2004 | Cox et al. |
| 6,682,476 B2 | 1/2004 | Alferness et al. |
| 6,689,048 B2 | 2/2004 | Vanden Hoek et al. |
| 6,695,769 B2 | 2/2004 | French et al. |
| 6,702,732 B1 | 3/2004 | Lau et al. |
| 6,723,041 B2 | 4/2004 | Lau et al. |
| 6,727,316 B1 | 4/2004 | Bremser |
| 6,730,016 B1 | 5/2004 | Cox et al. |
| 6,755,779 B2 | 6/2004 | Vanden Hoek et al. |
| 6,881,185 B2 | 4/2005 | Vanden Hoek et al. |
| 6,893,392 B2 | 5/2005 | Alferness |
| 6,902,522 B1 | 6/2005 | Walsh et al. |
| 6,902,524 B2 | 6/2005 | Alferness et al. |
| 6,908,426 B2 | 6/2005 | Shapland et al. |
| 6,951,534 B2 | 10/2005 | Girard |
| 7,060,023 B2 | 6/2006 | French et al. |
| 7,081,086 B2 | 7/2006 | Lau et al. |
| 7,155,295 B2 | 12/2006 | Lau et al. |
| 7,163,507 B2 | 1/2007 | Alferness et al. |
| 7,189,203 B2 | 3/2007 | Lau et al. |
| 7,235,042 B2 | 6/2007 | Vanden Hoek et al. |
| 7,252,632 B2 | 8/2007 | Shapland et al. |

| | | | |
|---|---|---|---|
| 2002/0019580 | A1 | 2/2002 | Lau et al. |
| 2003/0229265 | A1 | 12/2003 | Girard et al. |
| 2004/0059181 | A1 | 3/2004 | Alferness |
| 2004/0210104 | A1* | 10/2004 | Lau et al. ................... 600/37 |
| 2005/0033109 | A1 | 2/2005 | Lau et al. |
| 2005/0059854 | A1 | 3/2005 | Vanden Hoek et al. |
| 2005/0059855 | A1 | 3/2005 | Lau et al. |
| 2005/0090707 | A1 | 4/2005 | Lau et al. |
| 2005/0171589 | A1 | 8/2005 | Lau et al. |
| 2005/0192474 | A1 | 9/2005 | Vanden Hoek et al. |
| 2005/0256368 | A1 | 11/2005 | Klenk et al. |
| 2005/0283042 | A1* | 12/2005 | Meyer et al. ................. 600/37 |
| 2005/0288715 | A1 | 12/2005 | Lau et al. |
| 2006/0009831 | A1 | 1/2006 | Lau et al. |
| 2006/0155165 | A1* | 7/2006 | Vanden Hoek et al. ........ 600/37 |
| 2006/0229490 | A1 | 10/2006 | Chin |
| 2006/0270896 | A1 | 11/2006 | Dietz et al. |
| 2007/0208211 | A1 | 9/2007 | Alferness et al. |
| 2007/0219407 | A1 | 9/2007 | Vanden Hoek et al. |
| 2007/0225547 | A1 | 9/2007 | Alferness et al. |

FOREIGN PATENT DOCUMENTS

| | | |
|---|---|---|
| DE | 38 31 540 | 4/1989 |
| DE | 295 17 393 | 3/1996 |
| EP | 0 280 564 | 8/1988 |
| EP | 0 303 719 | 2/1989 |
| EP | 0 557 964 | 9/1993 |
| GB | 2 209 678 | 5/1989 |
| JP | 60-203250 | 10/1985 |
| JP | 01-145066 | 6/1989 |
| JP | 2-271829 | 11/1990 |
| SU | 1009457 | 4/1983 |
| WO | WO 93/03685 | 3/1993 |
| WO | WO 96/16601 | 6/1996 |
| WO | WO 96/31175 | 10/1996 |
| WO | WO 98/14136 | 4/1998 |
| WO | WO 98/29041 | 7/1998 |
| WO | WO 98/35632 | 8/1998 |
| WO | WO 98/58598 | 12/1998 |
| WO | WO 99/44534 | 9/1999 |
| WO | WO 00/01306 | 1/2000 |
| WO | WO 00/02500 | 1/2000 |
| WO | WO 00/06026 | 2/2000 |
| WO | WO 00/06027 | 2/2000 |
| WO | WO 00/06028 | 2/2000 |
| WO | WO 00/16700 | 3/2000 |
| WO | WO 01/02500 | 1/2001 |
| WO | WO 01/67985 | 9/2001 |
| WO | WO 2006/023580 | 3/2006 |

OTHER PUBLICATIONS

Capomolla et al., "Dobutamine and nitroprusside infusion in patients with severe congestive heart failure: Hemodynamic improvement by discordant effects on mitral regurgitation, left atrial function, and ventricular function", *American Heart Journal*, pp. 1089-1098 (Dec. 1997).
Capouya et al., "Girdling Effect of Nonstimulated Cardiomyoplasty on Left Ventricular Function", *The Society of Thoracic Surgeons*, vol. 56, pp. 867-871 (1993).
Cohn, "The Management of Chronic Heart Failure", *The New England Journal of Medicine*, vol. 335, No. 7, pp. 490-498 (Aug. 15, 1996).
Colleta et al., "Prognostic value of left ventricular volume response during dobutamine stress echocardiography", *European Heart Journal*, vol. 18, pp. 1599-1605 (Oct. 1997).
deVries, G. et al., "A Novel Technique for Measurement of Pericardial Balloon," *Am. J. Physiol Heart Circ Physiol*, vol. 280, No. 6, pp. H2815-H2822 (Jan. 2001).
Guasp, "Una protesis contentiva para el tratamiento de la miocardiopatia dilatada" *Revista Espanola de Cardiologia*, vol. 51, No. 7, pp. 521-528 (1998). (Includes the English translation).
Hamilton, D. et al. "Static and Dynamic Operating Characteristics of a Pericardial Balloon," *J. Appl. Physiol.*, vol. 90, No. 4, pp. 1481-1488 (Apr. 2001).
Kass et al., "Reverse Remodeling From Cardiomyoplasty in Human Heart Failure", *Circulation*, vol. 91, No. 9, pp. 2314-2318 (May 1, 1995).
Levin et al., "Reversal of Chronic Ventricular Dilation in Patients With End-Stage Cardiomyopathy by Prolonged Mechanical Unloading", *Circulation*, vol. 91, No. 11, pp. 2717-2720 (Jun. 1, 1995).
Oh et al., "The Effects Of Prosthetic Cardiac Binding And Adynamic Cardiomyoplasty In A Model Of Dilated Cardiomyopathy", *The Journal of Thoracic and Cardiovascular Surgery*, vol. 116, No. 1, pp. 148-153 (Jul. 1998).
Paling, "Two-Bar Fabrics (Part-Set Threading)", *Warp Knitting Technology*, Columbine Press (Publishers) Ltd., Buxton, Great Britain, p. 111 (1970).
Vaynblat et al., "Cardiac Binding in Experimental Heart Failure", *Ann Thorac Surg*, vol. 64 (1997).
Vinereanu, et al., "Worsening Global Diastolic Dysfunction of the Left Ventricle is Associated with a Progressive Decline in Longitudinal Systolic Function", *European Journal of Heart Failure*, Aug. 7(5): 820-8 (2005).
U.S. Appl. No. 60/148,130 entitled, "Apparatus and Method for Endoscopic Pericardial Access", filed Aug. 10, 1999.
U.S. Appl. No. 60/150,737 entitled, "Longitudinal Mechanical Dilator for Vessel Harvesting", filed Aug. 25, 1999.
U.S. Appl. No. 09/635,345 entitled, "Apparatus and Methods for Subxiphoid Endoscopic Access", filed Aug. 9, 2000.
International Search Report and Written Opinion from international application No. PCT/US2007/072345, mailed Jul. 3, 2008, 11 pages.
Labrousse, Louis et al., "Implantation of a Cardiac Support Device by the 'Parachute-Like' Technique Through Sternal and Trans-Abdominal Approach", Abstract, 94 Programme of the 4th EACTS/ESTS Joint Meeting, Wednesday Sep. 28, 2005, Barcelona, Spain.
PCT International Search Report and Written Report, International Application No. PCT/US0783689, mailed Aug. 25, 2008, 13 pages.

\* cited by examiner

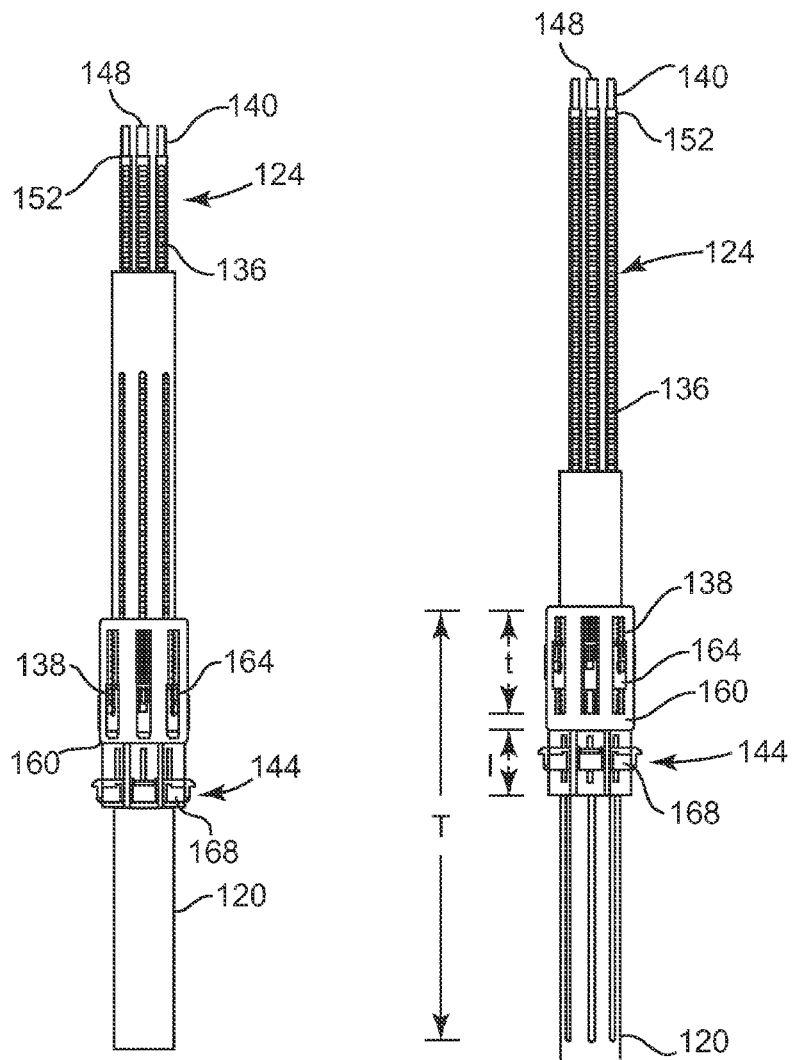
Fig. 2A
Fig. 2B
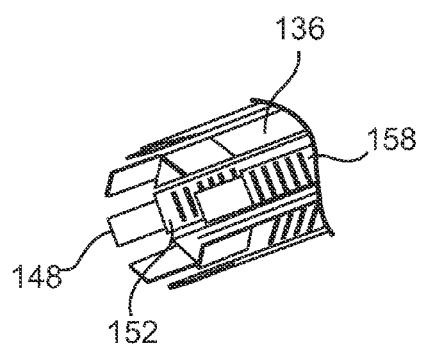
Fig. 2D
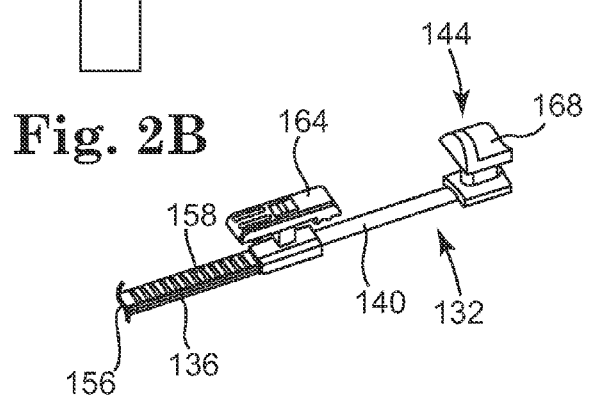
Fig. 2C

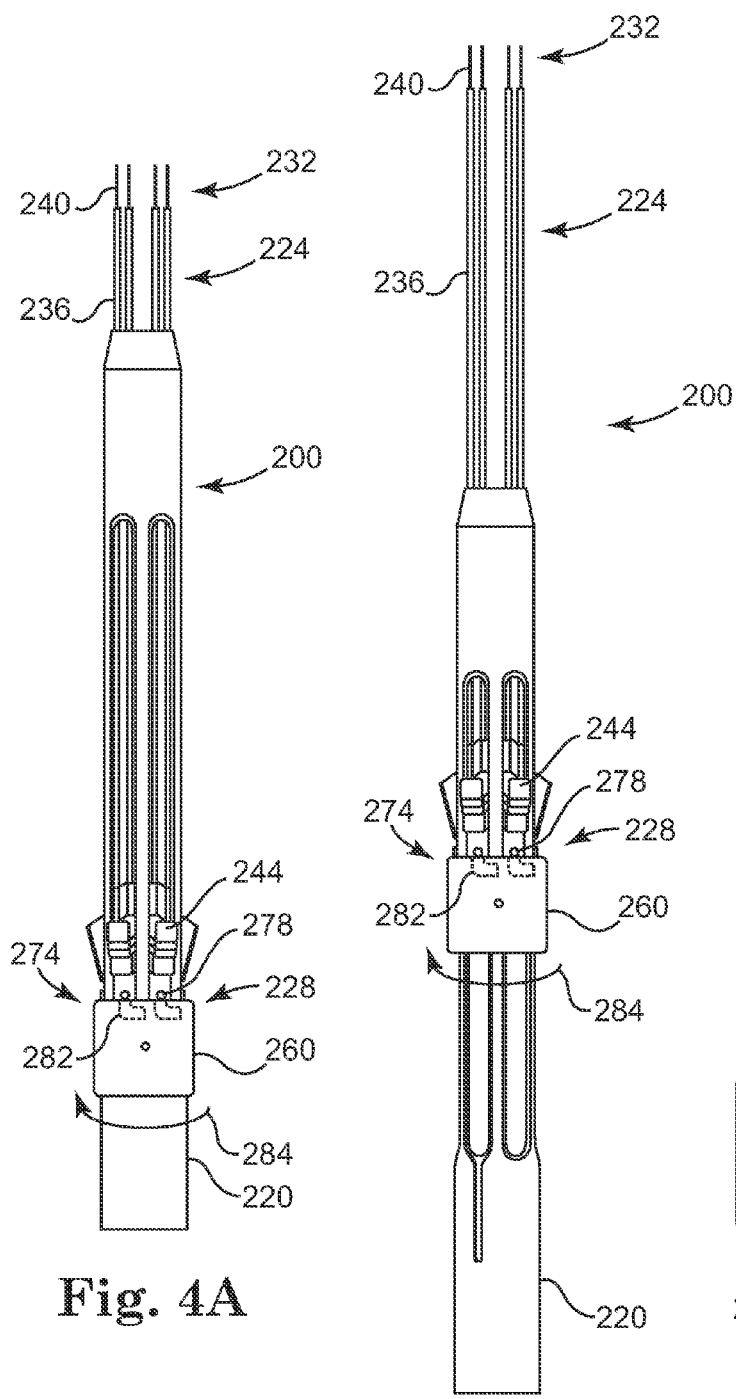

CARDIAC SUPPORT DEVICE DELIVERY TOOL WITH RELEASE MECHANISM

FIELD OF THE INVENTION

The present invention pertains to a method and apparatus for treating congestive heart disease and related valvular dysfunction. More particularly, the present invention is directed to an apparatus and method for delivery of a cardiac support device.

BACKGROUND OF THE INVENTION

Various cardiac support devices for treating congestive heart disease are known. One exemplary type of cardiac support device includes a cardiac jacket for reducing tension in the heart wall by constraining or resisting expansion of the heart. Devices and methods for delivering cardiac support devices using minimally invasive surgical procedures are also known. Such cardiac support devices and/or cardiac support device delivery devices are described, for example, in U.S. Pat. No. 5,702,343; U.S. Pat. No. 6,155,972; U.S. Pat. No. 6,193,648; U.S. Pat. No. 6,293,906; U.S. Pat. No. 6,482,146; U.S. Pat. No. 6,682,476; U.S. Pat. No. 6,902,524; U.S. Pat. No. 6,425,856; U.S. Pat. No. 6,908,426; U.S. Pat. No. 6,572,533; and U.S. Pat. No. 6,951,534, all of which are assigned to Acorn Cardiovascular, Inc. and are incorporated herein by reference.

Other embodiments of cardiac support devices and/or cardiac support device delivery devices are disclosed in U.S. Pat. No. 6,702,732; U.S. Pat. No. 6,723,041; U.S. patent application publication no. US 2006/0009831 A1 published Jan. 12, 2006; U.S. patent application publication no. US 2005/0288715 published Dec. 29, 2005; U.S. patent application publication no. US 2005/0256368 A1 published Nov. 17, 2005; U.S. patent application publication no. US 2005/0171589 published Aug. 4, 2005; U.S. patent application publication no. US 2005/0090707 A1 published Apr. 28, 2005; and U.S. patent application publication no. US 2005/0059855 A1 published Mar. 17, 2005, all of which are incorporated herein by reference.

There remains, however, a continuing need for improved delivery devices for cardiac support devices. In particular, there is a need for a delivery device for efficiently and effectively releasing the cardiac jacket over the heart.

SUMMARY OF THE INVENTION

In one embodiment, the present invention is an apparatus for placing a cardiac support device (CSD) on a heart. The apparatus includes a body, a deployment mechanism on the body for supporting the CSD in an open position for placement on the heart, and a release mechanism coupled to the deployment mechanism for releasably mounting the CSD to the deployment mechanism. The release mechanism includes a release element for releasably engaging the CSD, and a release actuator coupled to the release element for actuating the release element to release the CSD.

In another embodiment, the present invention is an apparatus for placing a cardiac support device (CSD) on a heart. The apparatus includes an elongate body, a deployment mechanism slidably coupled to the body for supporting the CSD, and a release means on the body for releasably coupling the CSD to the deployment mechanism.

In yet another embodiment, the present invention is a method for deploying a cardiac support device (CSD) about a heart of a patient. The method includes releasably coupling the CSD to a deployment mechanism of a delivery apparatus, positioning the CSD in a desired position about the heart using the delivery apparatus, and actuating a release mechanism to de-couple the CSD and the deployment mechanism. The release mechanism includes a release element coupled to the deployment mechanism and a release actuator coupled to the release element.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

BRIEF DESCRIPTION OF THE DRAWINGS

FIG. 2A shows a front view of the delivery device of FIG. 1 in a retracted state.

FIG. 2B shows a front view of the delivery device of FIG. 1 in an extended state.

FIG. 2C shows a perspective view of a portion of a control mechanism and release mechanism of FIG. 1.

FIG. 2D shows a perspective view of the distal ends of the support member and release element shown in FIG. 1.

FIG. 4A shows a front view of a delivery device according to another embodiment of the invention in a retracted state.

FIG. 4B shows a front view of the delivery device of FIG. 4A in an extended state.

FIG. 4C shows a side view of a portion of the control mechanism and release mechanism of FIG. 4A.

Figure 1:
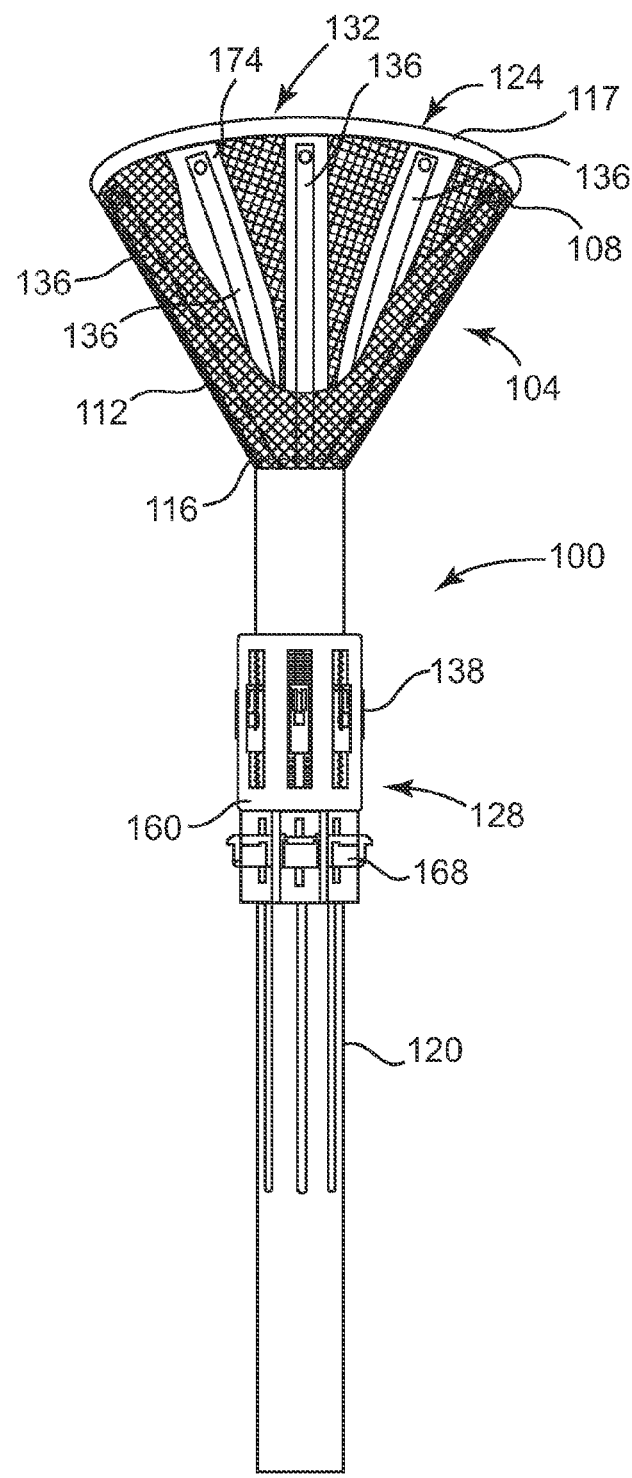
FIG. 1 shows a CSD mounted on an exemplary delivery device that can be used in relation to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION OF THE PREFERRED EMBODIMENTS

FIG. 1 illustrates a delivery device 100 according to one embodiment of the present invention supporting a cardiac support device (CSD) 104 for deployment over a patient's heart. The CSD 104 may be any type of cardiac support device, including, without limitation, any of the devices disclosed in any of the patents and patent publications referenced and incorporated herein in the Background of the Invention. In the illustrated embodiment, the CSD 104 includes an open base end 108 and an apex portion 112 having an open apex end 116. A hem 117 is formed about the open base end 108 of the CSD 104.

As shown in FIG. 1, the delivery device 100 includes a body 120, a deployment mechanism 124, an actuator or a control mechanism 128 on the body 120 operatively coupled to the deployment mechanism 124, and a release mechanism 132 (see FIG. 2C) on the body 120 for releasably coupling the CSD 104 to the deployment mechanism 124.

The deployment mechanism 124 is operable to move between a first retracted or closed state, as shown in FIG. 2A, and a second extended or open state, as shown in FIG. 1. FIG. 2B shows the deployment mechanism 124 moved to an extended but not opened state. The deployment mechanism 124 is further adapted to releasably support the CSD 104 and to accurately position the CSD 104 at a desired implantation position on the patient's heart. The deployment mechanism 124 includes at least one elongate support member 136. In the illustrated embodiment, the deployment mechanism 124 includes eight support members 136. The invention is not so limited, however, and the deployment mechanism 124 may include a greater or few number of support members 136 in varying configurations.

The control mechanism 128 drives the deployment mechanism 124 between the retracted and extended states for positioning the CSD 104 on the heart. In the illustrated embodiment, the control mechanism 128 is slidable along a portion of the length of the body 104 to move the support members 136 from the retracted state to the extended state. In the illustrated embodiment, the support members 136 are curved so that the support members 136 form a cup shape to receive the CSD 104 when in the extended state. In other embodiments (not shown), the control mechanism 128 also includes means for spreading apart or otherwise shaping the support members 136 when in the extended state.

The release mechanism 132 releasably couples the CSD 104 to the deployment mechanism 124. Thus, once the delivery device 100 has been manipulated to maneuver the CSD 104 into position over or about all or a portion of the heart, the release mechanism 132 is operated to release the CSD 104 from the delivery device 100 onto the heart. The release mechanism 132 includes a release element 140 (see FIG. 2A) for releasably engaging the CSD 104 and an actuator mechanism 144 operatively coupled to the release element 140 to control release of the CSD 104 from the release element 140.

In the illustrated embodiment, the release element 140 is an elongate member positioned adjacent to each of the support members 136. A distal end 148 of the release element 140 is movable from an engaged state in which the release element 140 permits the CSD 104 to be mounted to the deployment mechanism 124 and a released state in which the release element 140 releases the CSD 104 from the deployment mechanism 124. An actuator mechanism 144 is operable to move the release element 140 between the engaged and released states. In the illustrated embodiment, the release elements 140 slide through a channel 156 in the support members 136. The support members 136 are formed with a plurality of slots 158 to provide incremental advancement of the release elements 140 relative to the support members 136.

In the embodiment illustrated in FIGS. 1 and 2A-2D, the control mechanism 128 and the actuator mechanism 144 are integrated into a cylinder 160 positioned about the body 120.

The cylinder 160 slides over a first or main travel region T while moving the all of the support members 136 from the retracted state to the extended state. A second control mechanism 138 including a first user interface 164 is provided for moving individual support members 136 from the retracted state to the extended state. The first user interfaces 164 are individually slidable over a second or supplementary travel region t to move the support members 136. The release elements 140 remain in the engaged state while the support members 136 are moved from the retracted state to the extended state.

The actuator mechanism 144 is actuated by sliding a second user interface 168 coupled to the support elements 140 over a third or individual travel region I to move the release elements 140 between engaged and released states. In the illustrated embodiment, the actuator mechanism 144 is operable to actuate the release elements 140 individually. In other embodiments, however, two or more, or all, of the release elements 140 may be actuated as a group.

Figure 3A:
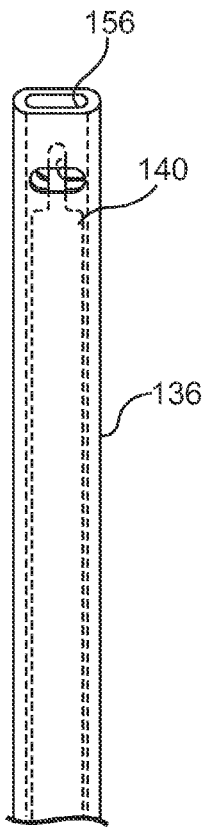
FIG. 3A shows a front view of the release element in relation to the support member of FIG. 1.

As illustrated generally in FIG. 3A, the CSD 104 includes a release structure 170 releasably engaged by one or both of the deployment mechanism 124 and the release element 140. The release structure 170 is adapted for coupling to the deployment mechanism 124 for facilitating release of the CSD 104 from the deployment mechanism 124. In addition, some embodiments of the CSD 104 includes a lubricious element 174. Lubricious element 174 can also be releasably coupled to the CSD 104 by the release mechanism 132. Specifically, the release mechanism 132 is operable to de-couple at least a portion of the lubricious element 174 from the CSD 104.

Figure 3B:
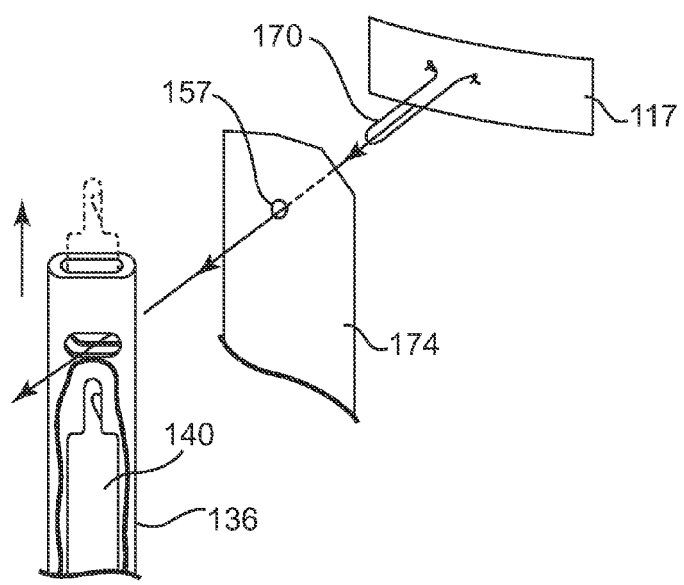
FIG. 3B shows the release element and support member of FIG. 3A in relation to a portion of the CSD shown in exploded detail.

FIG. 3B illustrates the release element 140 in more detail. The release element 140 is in the form of a hook. A release structure 170 in the form of a loop of cord or suture is coupled to the hem 117 of the CSD 104. In the engaged state, the release structure 170 is coupled to the release element 140 through a hole 157 in the lubricious element 174.

The CSD 104 is placed over a patient's heart with the device 100 as follows. The CSD 104 is mounted to the deployment mechanism 124 with the release elements 140 in the engaged state. The deployment mechanism 124 is put into the retracted state as shown in FIG. 2A. The delivery device body 120 is manipulated to position the CSD 104 near the heart. The user slides the cylinder 160 distally over the body 120, advancing the support members 136 from the retracted state to the extended state while the release elements 140 remain in the engaged state. The user may actuate the first user interfaces 164 to move the support members 136 between the retracted and extended states individually to more precisely position the CSD 104 about the heart.

Once the CSD 104 is maneuvered into the desired position, the actuator mechanisms 144 are actuated by sliding the second user interfaces 168 to move the release elements 140 from the engaged state to the released state to release the CSD 104 from the delivery device 100. In the engaged state, the release element 140 is retracted within the channel 156 such that the release structure 170 coupled to the release element 140. Upon movement of the release element 140 to the released state, shown in dashed lines, the release structure 170 is released from the support member 136.

FIGS. 4A-4C, 5A-5D, 6A-6C and 7A-7B illustrate various additional embodiments of the control mechanism 128 and actuator mechanism 144. FIGS. 8A-8B, 9A-9B, 10A-10B, 11A-11C, 12A-12C, 13A-13D and 14A-14C illustrate various additional embodiments of the release element 140 and release structure 170. The various embodiments of the control mechanism 128 and actuator mechanism 140 described with respect to FIGS. 1, 2A-2D, 3A-3B, 4A-4C, 5A-5D, 6A-6C and 7A-7B may be used in an combination with the various embodiments of the release element 140 and release structure 170 described with respect to FIGS. a, 2A-2D, 3A-3B, 8A-8B, 9A-9B, 10A-10B, 11A-11C, 12A-12C, 13A-13D and 14A-14C.

FIGS. 4A-4C illustrate a delivery device 200 according to another embodiment of the invention showing an alternate release mechanism. As shown in FIG. 2A, the delivery device 200 includes a body 220, a deployment mechanism 224, a control mechanism 228 on the body 220 operatively coupled to the deployment mechanism 224, and a release mechanism 232 on the body 220 for releasably coupling a CSD (not shown) to the deployment mechanism 224.

Similar to previously described embodiments, advancing a cylinder 260 actuates the control mechanism 228, moving the deployment mechanism 224 from a retracted state as shown in FIG. 4A to an extended state as shown in FIG. 4B. In the illustrated embodiment, the control mechanism 228 is further provided with a locking feature 274 for locking individual advancement of the support members 236. The locking feature 274 includes protrusions 278 and keyways 282 formed in the cylinder 260. Rotation of the cylinder 260, as indicated by arrow 284, captures the protrusions 278 in the keyways 282, preventing individual advancement of the support members 236.

The release mechanism 232 includes a release element 240 and an actuator mechanism 244. The actuator mechanism 244 includes a tilting lever arm 286 coupled to a mechanical linkage 290. Tilting the lever arm 286 forward, as indicated by arrow 292, pulls the linkage 290 proximally to move the release elements 240 from an engaged state to a released state. The lever arm 286 is also part of the control mechanism 228 and functions as a user interface for advancing the support members 236 individually.

Figures 5A, 5B, 5C:
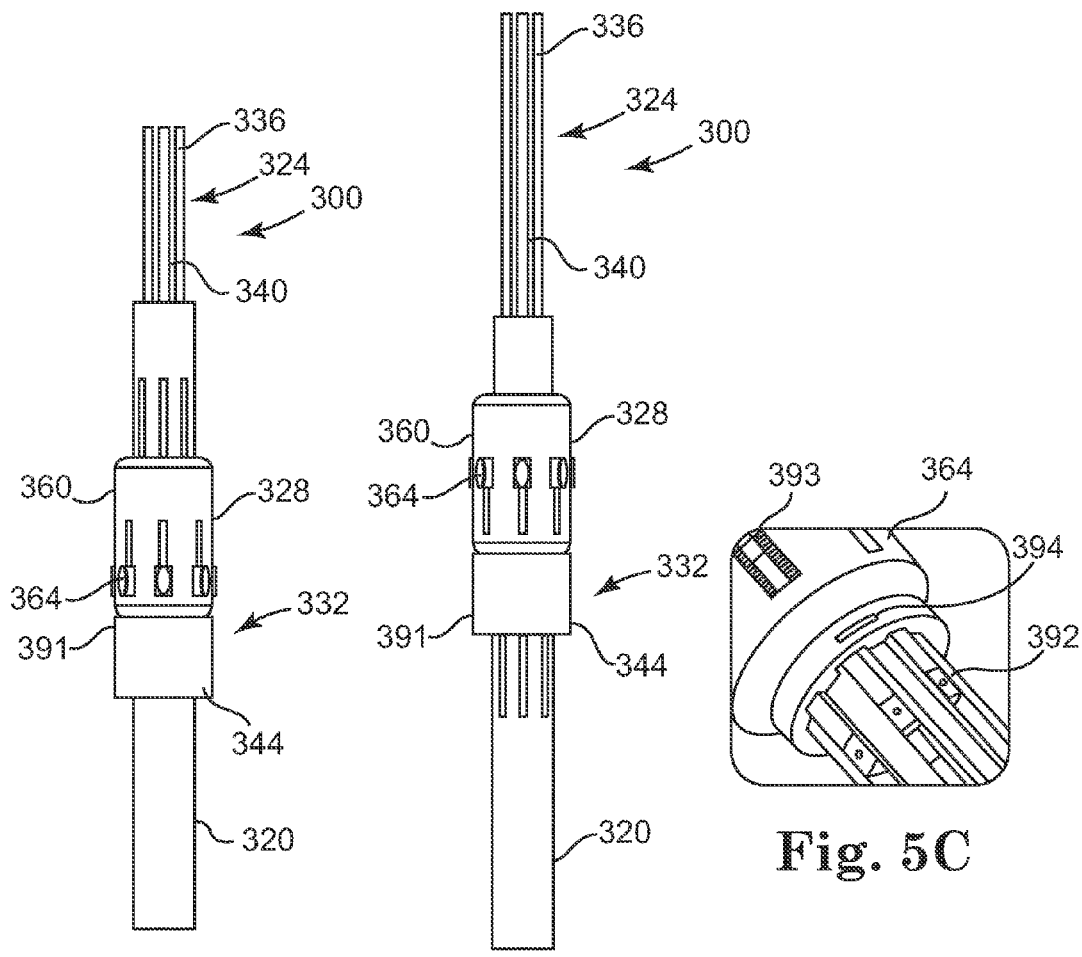
FIG. 5A shows a front view of a delivery device according to another embodiment of the invention in a retracted state.
FIG. 5B shows a front view of the delivery device of FIG. 5A in an extended state.
FIG. 5C shows a perspective view of a portion of the release mechanism of FIG. 5A.
Figure 5D:
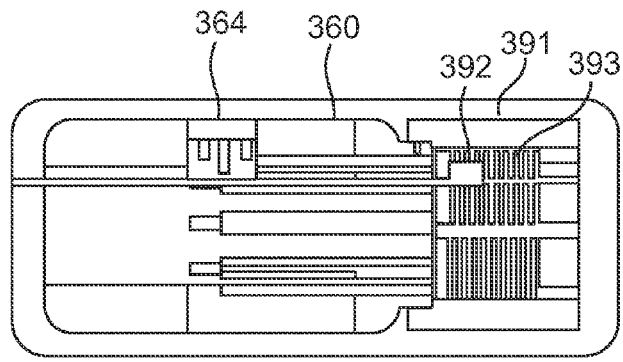
FIG. 5D shows a cross sectional view of a portion of the control mechanism and release mechanism of FIG. 5A.

FIGS. 5A-5D illustrate a delivery device 300 according to another embodiment of the invention showing an alternate release mechanism. As shown in FIG. 5A, the delivery device 300 includes a body 320, a deployment mechanism 324, a control mechanism 328 on the body 320 operatively coupled to the deployment mechanism 324, and a release mechanism 332 on the body 320 for releasably coupling a CSD (not shown) to the deployment mechanism 324.

Similar to previously described embodiments, advancing a cylinder 360 actuates the control mechanism 328, moving the deployment mechanism 324 from a retracted state as shown in FIG. 5A to an extended (but not opened) state as shown in FIG. 5B. The control mechanism 324 further includes user interface buttons 364 for individually advancing the support members 336 and release elements 340.

The release mechanism 332 includes a release element 340 and an actuator mechanism 344. The actuator mechanism 344 includes a rotating actuator cylinder 391 that is coupled to all of the release elements 340. The actuator mechanism 344 is operable to move all of the release elements 340 from an engaged state to a release state in unison upon rotation of the actuator cylinder 391. The release elements 340 each have an engagement pin 392 that is synchronized with axial teeth 393 in the actuator cylinder 391. Rotational movement of the actuator cylinder 391 captures the engagement pins 392 at various positions of individual adjustment of the support members 336. A keyway 394 in the cylinder 360 controls rotation and forward movement of the actuator cylinder 391.

Figures 6A, 6B, 6C:
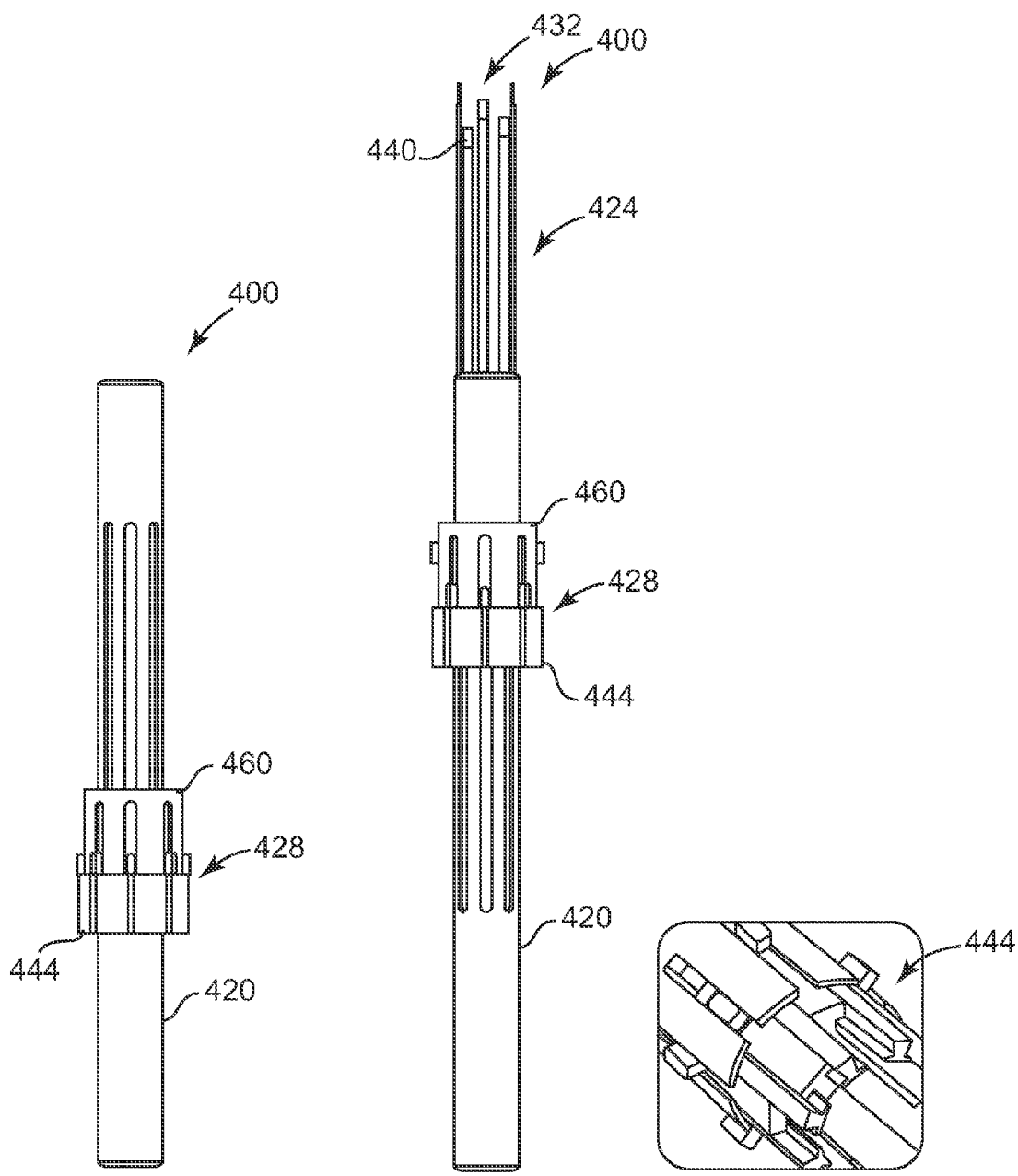
FIG. 6A shows a front view of a delivery device according to another embodiment of the invention in a retracted state.
FIG. 6B shows a front view of the delivery device of FIG. 6A in an extended state.
FIG. 6C shows a perspective view of a portion of the release mechanism of FIGS. 6A and 6B.

FIGS. 6A-6C illustrate another embodiment of a delivery device 400 showing an alternative release mechanism. As shown in FIG. 6A, the delivery device 400 includes a body 420, a deployment mechanism 424, a control mechanism 428 on the body 420 operatively coupled to the deployment mechanism 424, and a release mechanism 432 on the body 420 for releasably coupling a CSD (not shown) to the deployment mechanism 424.

The release mechanism 432 includes a release element 440 and an actuator mechanism 444. Similar to previously described embodiments, advancing a cylinder 460 actuates the control mechanism 424, moving the deployment mechanism 424 from a retracted state as shown in FIG. 6A to an extended state as shown in FIG. 6B.

Figure 7A:
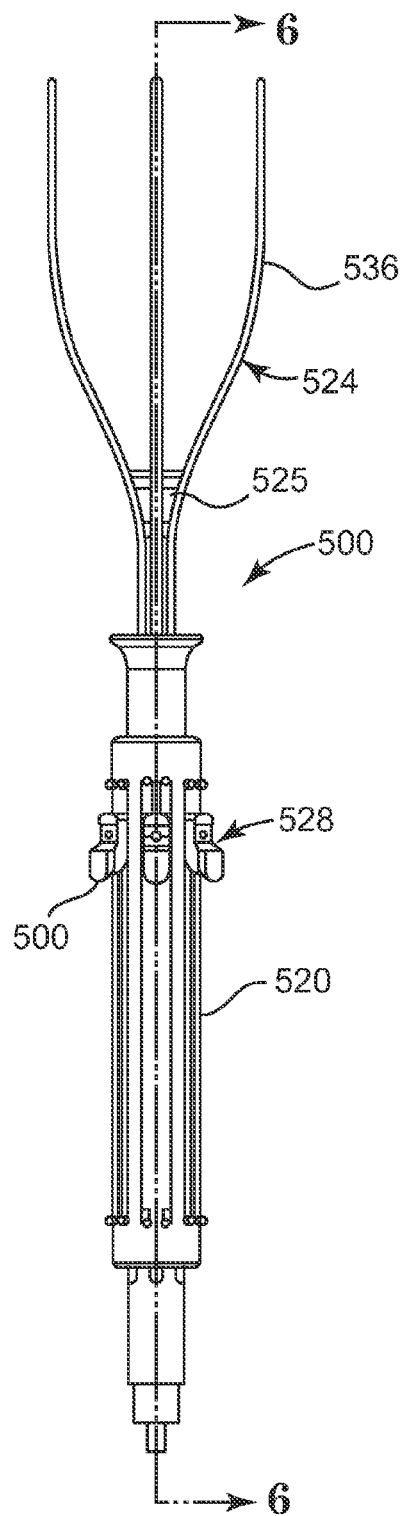
FIG. 7A shows a front view of a delivery device according to another embodiment of the invention in an extended state.
Figure 7B:
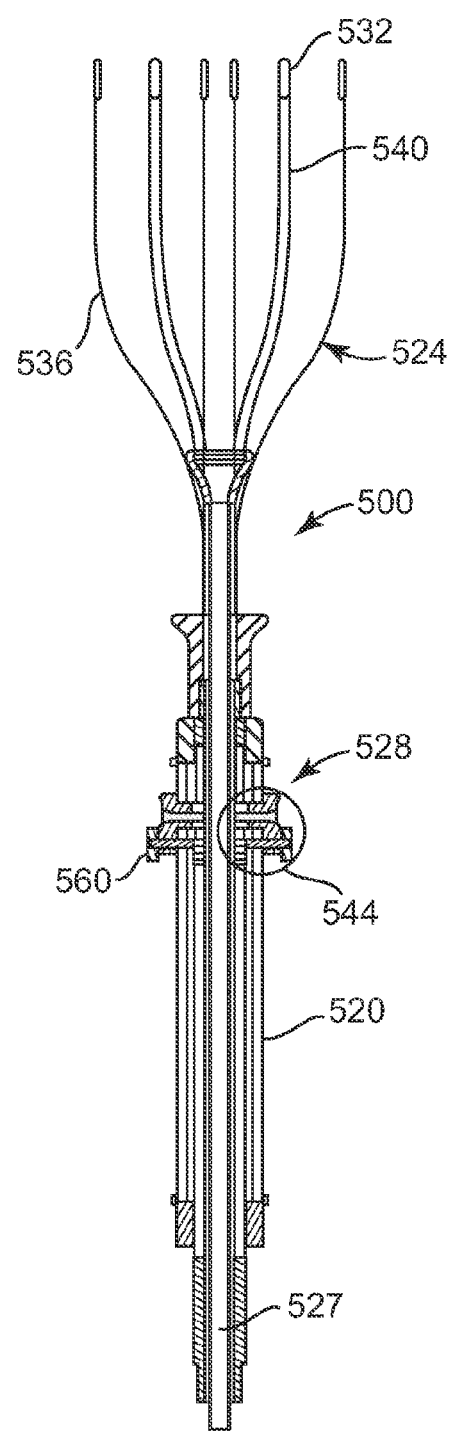
FIG. 7B shows a cross-sectional view of the delivery device of FIG. 7A taken along line 6-6.

FIGS. 7A and 7B illustrate another embodiment of a delivery device 500 showing an alternative release mechanism. As shown in FIG. 7A, the delivery device 500 includes a body 520, a deployment mechanism 524, a control mechanism 528 on the body 520 operatively coupled to the deployment mechanism 524, and a release mechanism 532 on the body 520 for releasably coupling a CSD (not shown) to the deployment mechanism 524. A suction cup 525 for releasably engaging a patient's heart is connected to a vacuum source (not shown) though tube 527. Actuator mechanism 544 is operated in a manner similar to that of the above-described embodiments to move the deployment mechanism 524 from a retracted position (not shown) to the extended and open position shown in FIGS. 7A and 7B. The support members 536 can be formed resilient members, and can be guided at least in part from their retracted positions to the extended and open positions shown in FIGS. 7A and 7B by the suction cup 525.

Figure 8A:
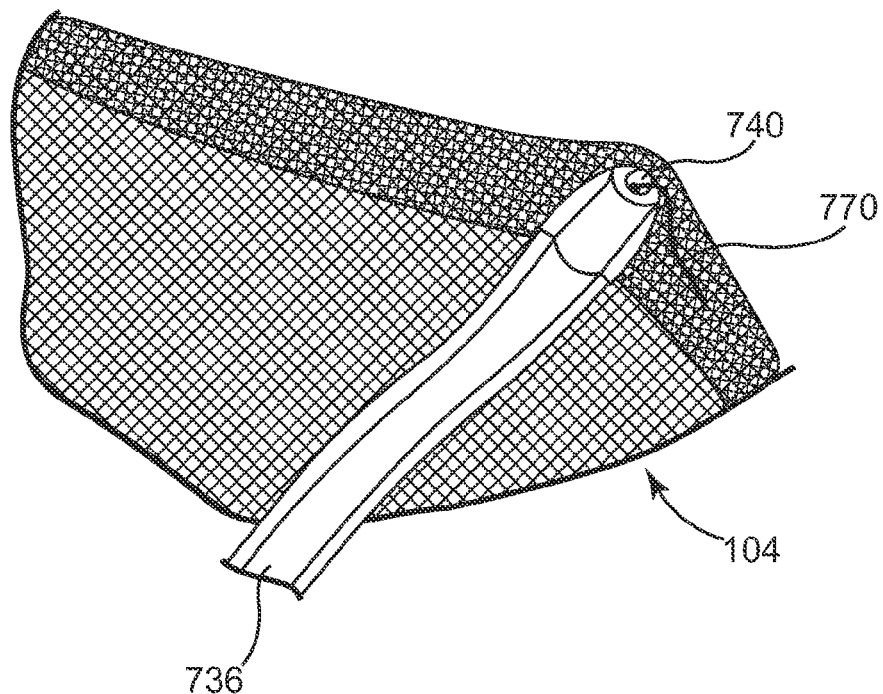
FIG. 8A shows a release element and support member according to another embodiment of the present invention coupled to a CSD.
Figure 8B:
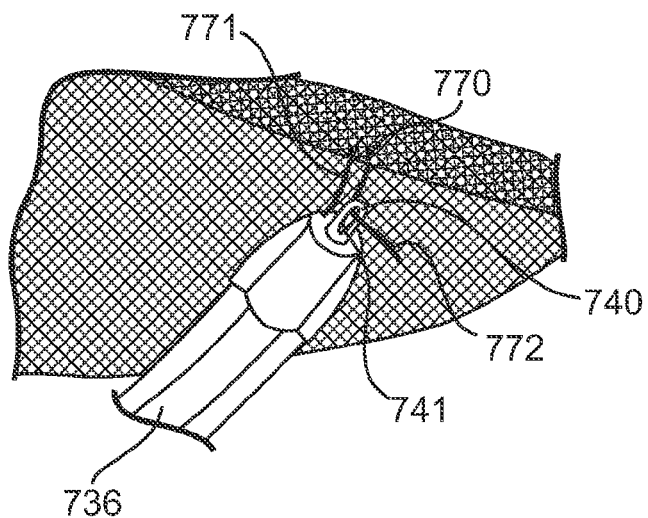
FIG. 8B shows the release element and support member of FIG. 8A released from the CSD.

FIGS. 8A and 8B illustrate a support member 736, release element 740 and release structure 770 according to another embodiment of the invention. The release element 740 includes an opening 741. The release structure 770 is in the form of a loop of cord or suture that is threaded through a portion of the CSD 104, with a first end 771 coupled to the delivery device 100 and a second end 772 that is free. When the release element 740 is in the engaged state, as shown in FIG. 8A, the free end 772 of the release structure 770 is inserted through the hole 741 and the release element 740 is retracted within the support member 736. The free end 772 of the release structure 770 is thus captured between the release element 740 and the support member 736, coupling the CSD 104 to the support member 736. When the release element 740 is moved to the released state, shown in FIG. 8B, the release element 740 is advanced distally relative to the support member 736, releasing the release structure 770. The release structure 770 is easily pulled through the hole 741 and the CSD 104 as the support member 736 is withdrawn.

Figure 9A:
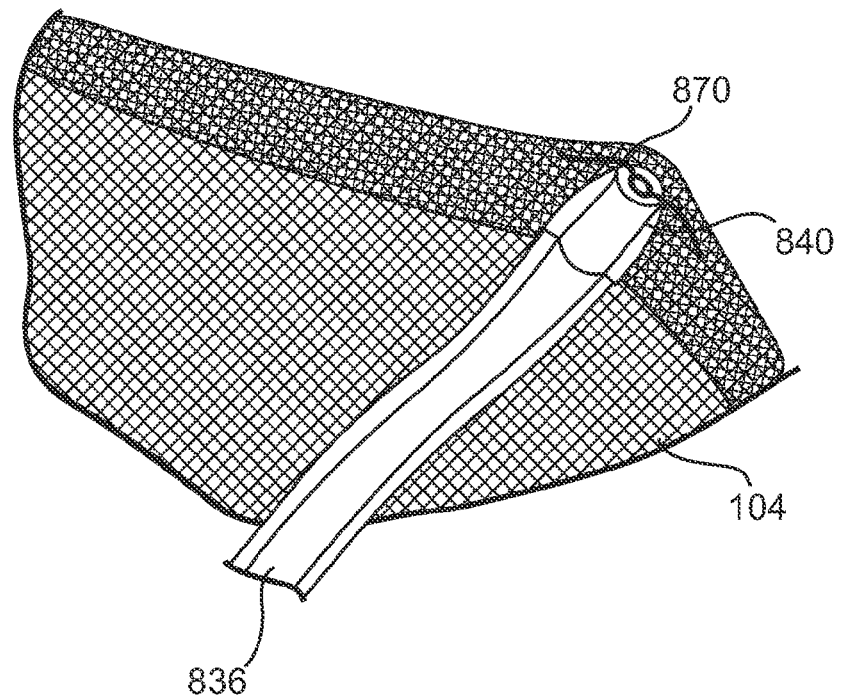
FIG. 9A shows a release element and support member according to another embodiment of the present invention coupled to a CSD.
Figure 9B:
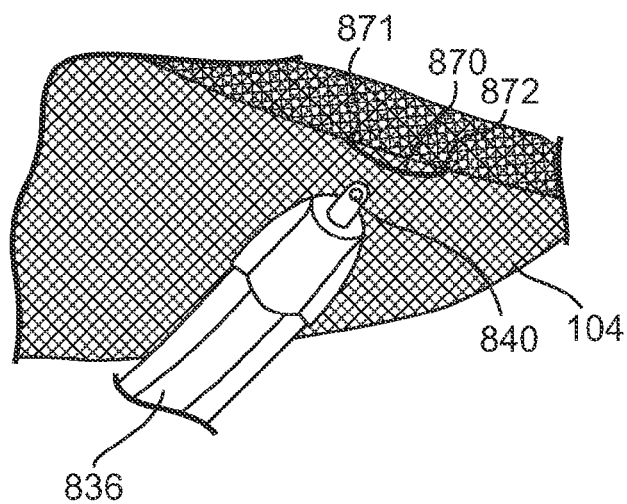
FIG. 9B shows the release element and support member of FIG. 9A released from the CSD.

FIGS. 9A and 9B illustrate a release element 840 and release structure 870 according to another embodiment of the present invention. The release element 840 is in the form of a hook. The release structure 870 is in the form of a loop of cord or suture having ends 871, 872 coupled to the CSD 104. The release structure 870 is captured by the hook of the release element 840 and coupled to the support member 836 when the release element 840 is in the engaged state, as shown in FIG. 9A. When the release element 840 is moved to the released state, as shown in FIG. 9B, the release structure 870 is released to de-couple the support member 836 and the CSD 104.

Figure 10A:
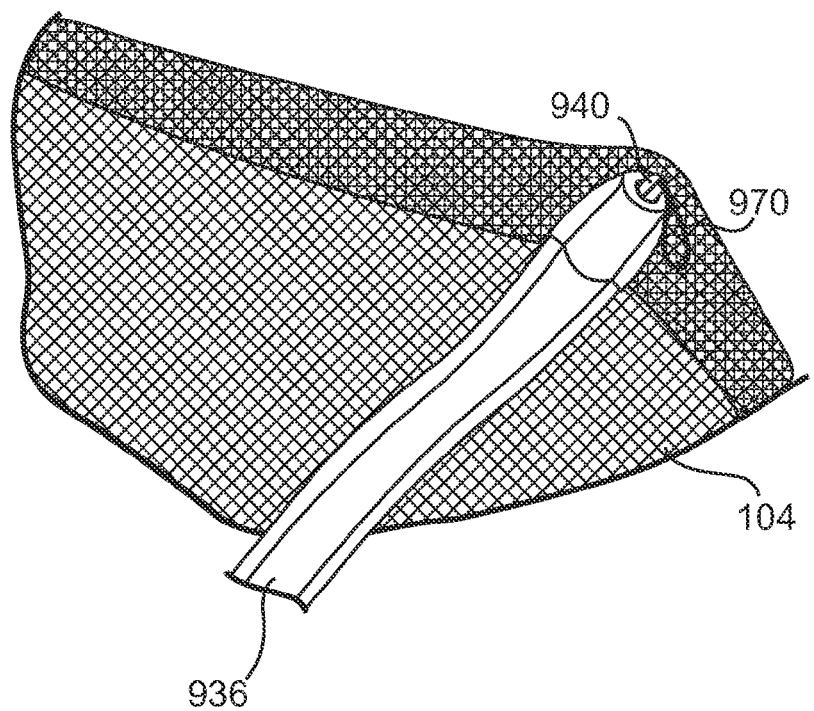
FIG. 10A shows a release element and support member according to another embodiment of the present invention coupled to a CSD.
Figure 10B:
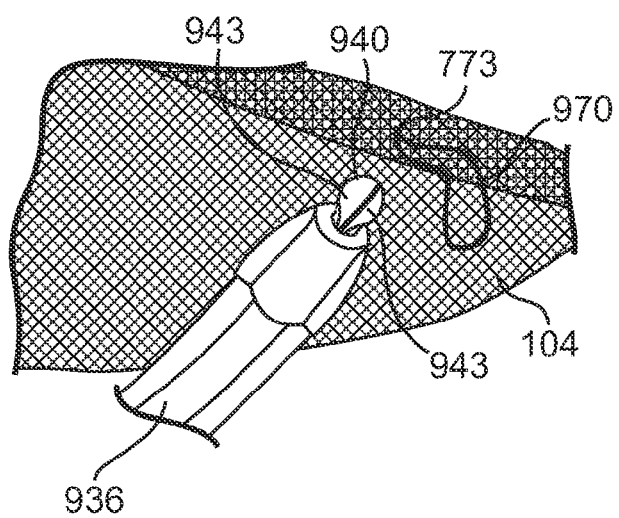
FIG. 10B shows the release element and support member of FIG. 10A released from the CSD.

FIGS. 10A and 10B illustrate a release element 940 and release structure 970 according to another embodiment of the present invention. The release element 940 is in the form of a pair of pincers 943, while the release structure 970 is in the form of a loop of cord or suture having a portion 773 coupled to the CSD 104. When the release element 932 is in the engaged state, the release element 932 is retracted within the support member 936, causing the pincers 943 to be pinched together, thus capturing the release structure 970, as shown in FIG. 10A. When the release element 940 is moved to the released state, as shown in FIG. 10B, the release structure 970 is advanced distally relative to the support member 936 and the pincers 943 spread apart to release the release structure 970.

Figure 11A:
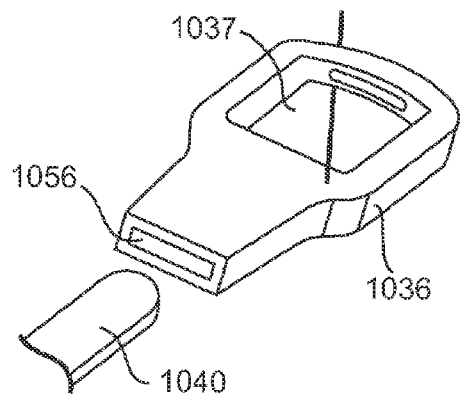
FIG. 11A shows a portion of a release mechanism according to another embodiment of the invention.
Figure 11B:
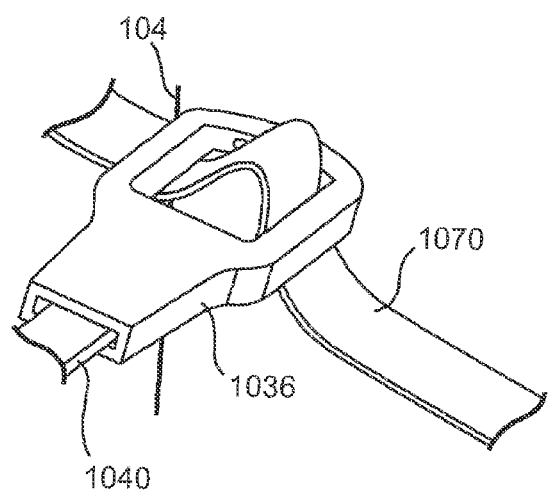
FIG. 11B shows the release mechanism of FIG. 11A coupled to a portion of a CSD.
Figure 11C:
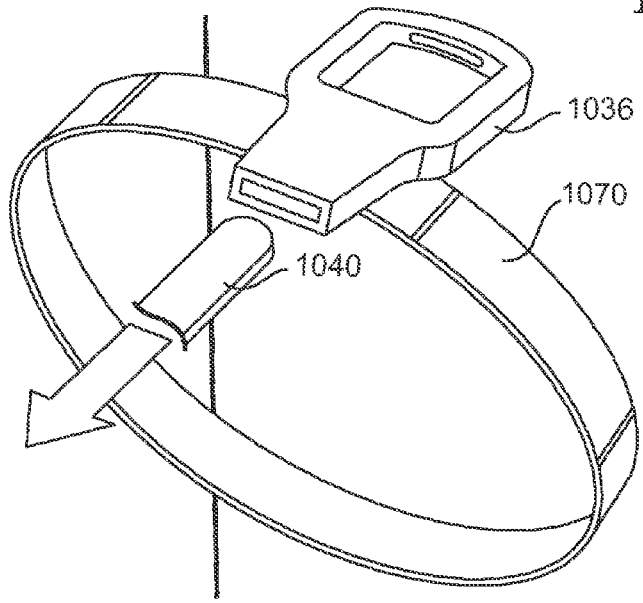
FIG. 11C shows the release mechanism of FIG. 11B de-coupled from the CSD.

FIGS. 11A-11C illustrate a support member 1036, release element 1040 and release structure 1070 configuration according to another embodiment of the present invention. The release element 1040 is in the form of a flat rod received within a channel 1056 formed by the support member 1036. A distal end of the support member 1036 includes an opening 1037. The release structure 1070 is in the form of a flexible band formed around at least a portion of the CSD 104. In the engaged state, the release structure 1070 is received in the opening 1037 and held in place by the release element 1040 which is positioned at the opening 1037 (see FIG. 11B). Upon movement of the release element 1040 from the engaged state, shown in FIG. 11B, to the release state, shown in FIG. 11C, the release element 1040 is moved proximally within the channel 1057 to release the release structure 1070 from the support member 1036.

Figure 12A:
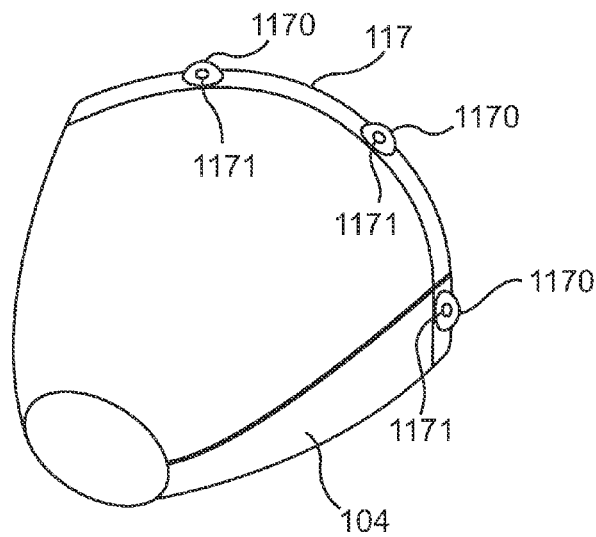
FIG. 12A shows a CSD having a release structure according to one embodiment of the invention.
Figure 12B:
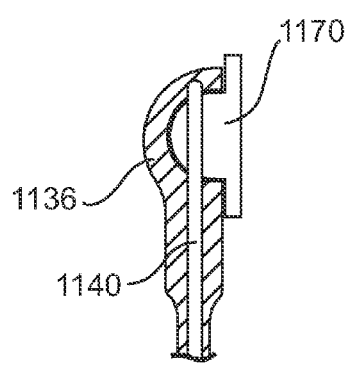
FIG. 12B shows a release mechanism according to one embodiment of the present invention in relation to the CSD of FIG. 12A.
Figure 12C:
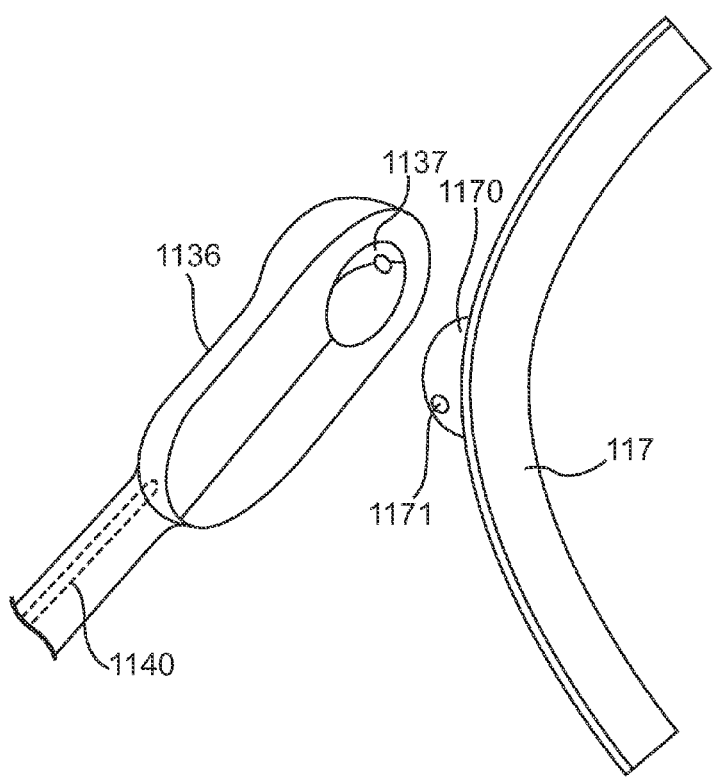
FIG. 12C shows a side-sectional view of the CSD of FIG. 12A coupled to the release mechanism.
Figure 13A:
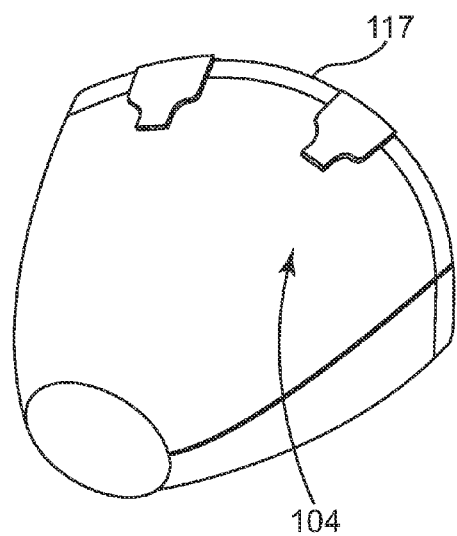
FIG. 13A shows a CSD having a release structure according to yet another embodiment of the invention.
Figure 13B:
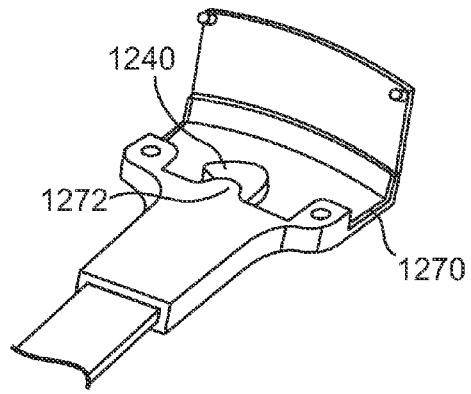
FIG. 13B shows the release structure of FIG. 13A and a release mechanism according to one embodiment of the invention.
Figure 13C:
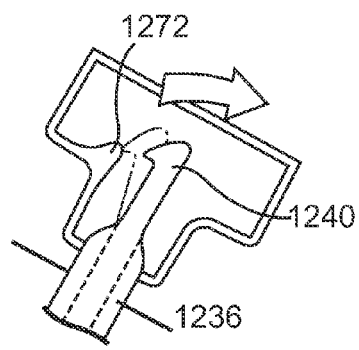
FIG. 13C shows the actuation of the release mechanism within the release structure shown in FIG. 13A.
Figure 13D:
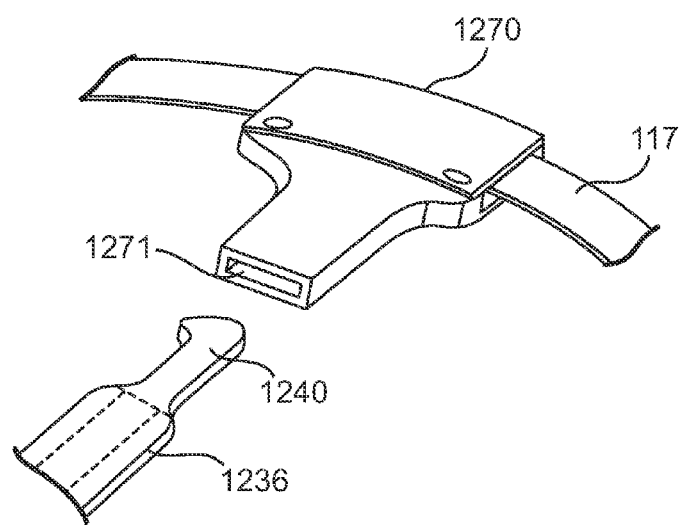
FIG. 13D shows the release mechanism de-coupled from the release structure of FIG. 13A.

FIGS. 12A-12C illustrate a support member 1136, release element 1140 and release structure 1170 according to another embodiment of the invention. The release structure 1170 is in the form of protrusions on the hem 117 of the CSD 104 and each has an opening 1171 therethrough (see FIG. 12A). As shown in FIG. 12C, the support member 1136 has a distal recess 1137 sized and shaped to receive the release structure 1170. The release element 1140 is in the form of a slender rod sized to be received in the opening 1171. In the engaged state, shown in FIG. 12B, the release structures 1170 are positioned within the recesses 1137 and the release elements 1140 are inserted into the openings 1171 to hold the release structures 1170 in place. Upon movement of the release element 1140 from the engaged state, to the release state, shown in dashed lines in FIG. 12C, the release element 1140 is withdrawn proximally out of the opening 1171 to release the release structure 1170 from the recesses 1137.

FIGS. 13A-D illustrate a release element 1240, support member 1236 and release structure 1270 according to another embodiment of the invention. The release structure 1270 is in the form of a lock housing positioned on the hem 117 of the CSD 104. A hook 1272 is formed within the release structure 1270. The release structure 1270 further has a passageway 1271 for receiving the release element 1240. In the engaged state, shown in FIG. 13B (release structure shown opened for clarity), the release element 1240 is captured on the hook 1272. Upon movement of the release element 1240 from the engaged state, shown in solid lines in FIG. 13C, to a release state, shown in dashed lines, the release element 1240 disengages from the hook 1272, allowing the release element 1240 to be withdrawn proximally through the passageway 1271 (see FIG. 13D).

Figure 14A:
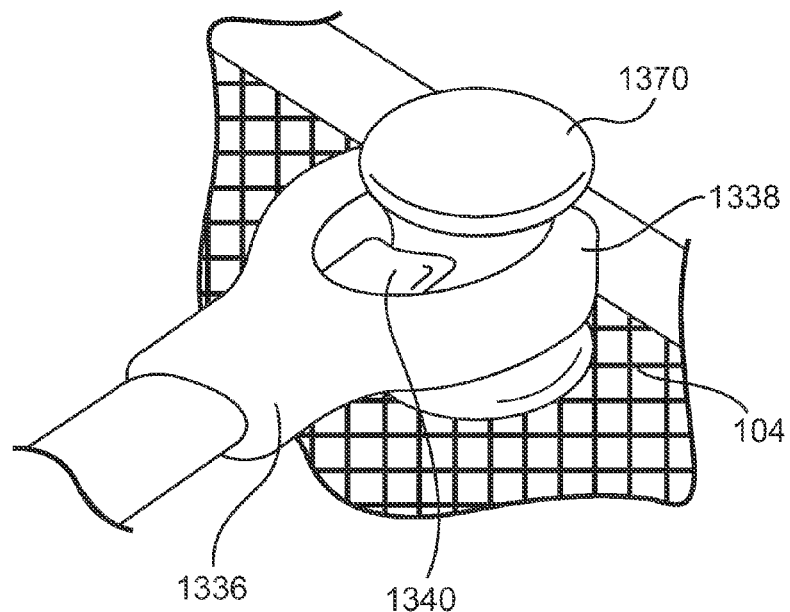
FIG. 14A shows a release structure and release mechanism according to another embodiment of the present invention.
Figure 14B:
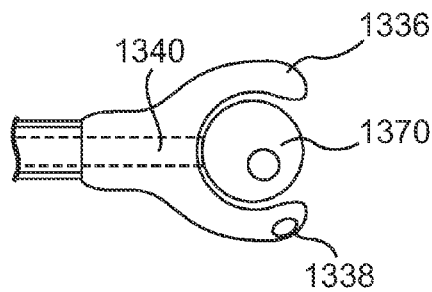
FIG. 14B shows a front view of the release mechanism coupled to the release structure of FIG. 14A.
Figure 14C:
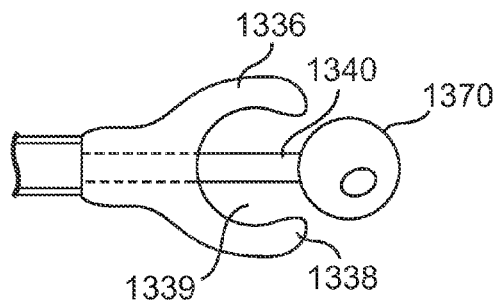
FIG. 14C shows a front view of the release mechanism de-coupled from the release structure shown in FIG. 14B.

FIGS. 14A-14C illustrate a release element 1340, support member 1336 and release structure 1370 according to another embodiment of the invention. The support member 1336 includes a U-shaped yoke 1338 defining an opening 1339. The release element 1340 is movable from an engaged state, in which the release element 1340 is proximal to the opening 1339 (see FIG. 14B), to a release state, in which the release element 1340 is positioned within the opening 1339 (see FIG. 14C). The release structure 1370 is in the form of a projection sized and shaped to be snugly received within the yoke 1338. Movement of the release element 1340 from the engaged state, shown in FIG. 14B, to the release state, shown in FIG. 14C, ejects the release structure 1370 from the yoke 1338.

Figure 15A:
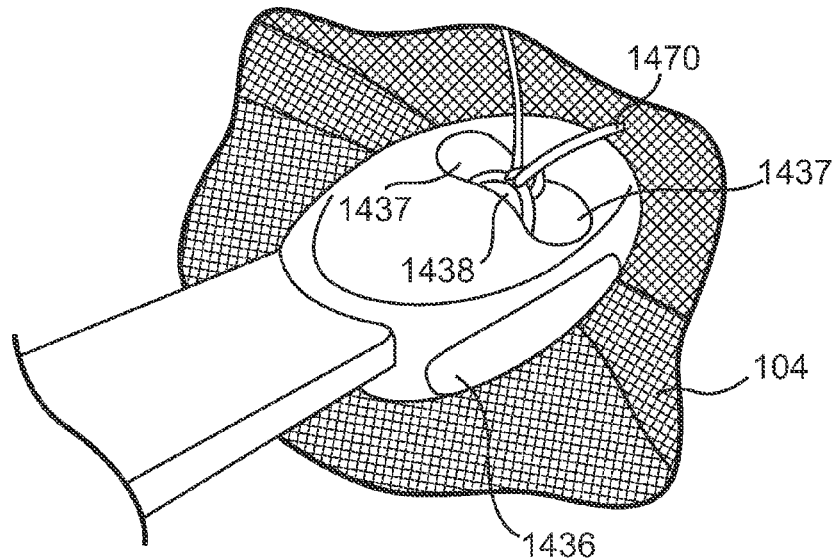
FIG. 15A shows a portion of a release mechanism releasably coupled to a CSD according to another embodiment of the invention.
Figure 15B:
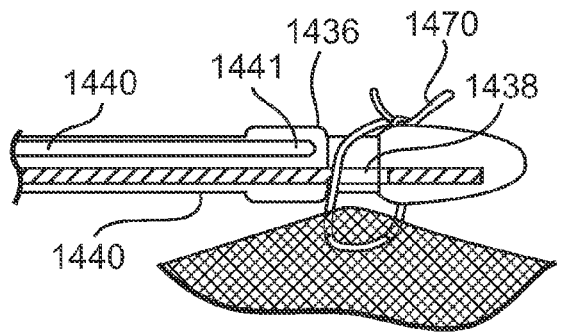
FIG. 15B shows a side view of the release mechanism and CSD of FIG. 15A.
Figure 15C:
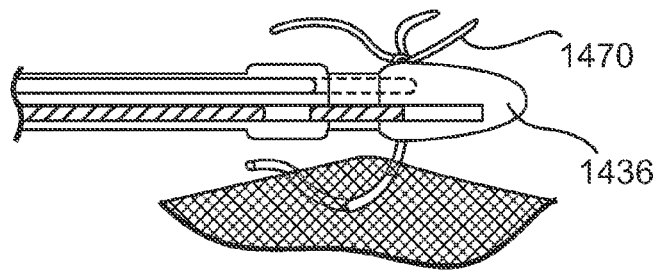
FIG. 15C shows a side view of the release mechanism of FIG. 15B released from the CSD.

FIGS. 15A-15C illustrate a portion of a release element 1440, support member 1436 and release structure 1470 according to another embodiment of the invention. The release structure 1470 is in the form of a length of cord or suture that is threaded through the CSD 104. The support member 1436 includes a pair of distal openings 1437 divided by a support bridge 1438. The release element 1440 includes a cutting surface 1441. In the engaged state, shown in FIGS. 15A and 15B, the release element 1440 is positioned proximally to the openings 1437. The release structure 1470 is threaded through the openings 1437 and tied over the bridge 1438 to couple the CSD 104 to the support member 1436. Upon movement of the release element 1440 to the release state, shown in FIG. 15C, the release element 1440 is moved distally over the release structure 1470 to cut the release structure 1470, thus releasing the CSD 104 from the support member 1436.

Figure 16A:
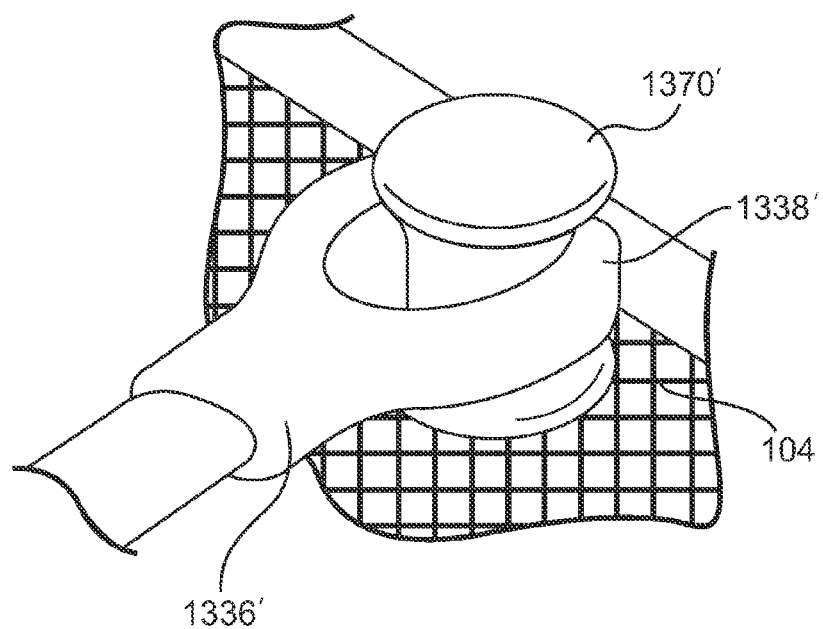
FIG. 16A shows a release structure and release mechanism according to another embodiment of the present invention.
Figure 16B:
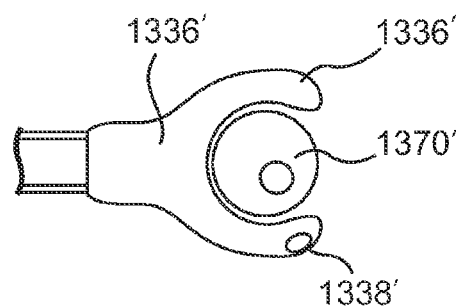
FIG. 16B shows a front view of the release mechanism coupled to the release structure of FIG. 16A.
Figure 16C:
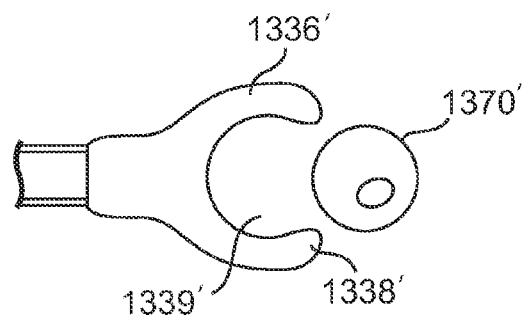
FIG. 16C shows a front view of the release mechanism de-coupled from the release structure shown in FIG. 16B.

FIGS. 16A-16C illustrate a support member 1336' and release structure 1370' according to another embodiment of the invention. The support member 1336' and release structure 1370' can be substantially the same or similar to support member 1336 and release structure 1370 described above in connection with FIGS. 14A-14C, and similar features are identified by similar reference numbers. Unlike the embodiment of the invention shown in FIGS. 14A-14C, the embodiment shown in FIGS. 16A-16C does not include a release element 1340. Instead and as described in greater detail below, support member 1336' is passively disengaged from the release structure 1370'. The support member 1336' includes a C- or U-shaped yoke 1338' defining an opening 1339'. The release structure 1370' is in the form of a projection sized and shaped to be snugly received within the yoke 1338'. Yoke 1338' is formed of resilient material that enables the yoke to sufficiently deform and "snap" onto the release structure 1370' (e.g., to diametrically expand and then return to its original shape). The characteristics of the yoke 1338' in cooperation with the release structure 1370' provides sufficient strength to enable the yoke to remain attached to the release structure while CSD 104 is positioned on the patient's heart. Following positioning of the CSD 104, movement of the support member 1336' in a direction opposite the opening in the yoke 1338' causes the yoke to deform and disengage from the release structure 1370'. The support member 1336' is thereby passively released from the CSD 104 since it was the motion of the support member itself, rather than another structure, that causes the release action.

Figure 17:
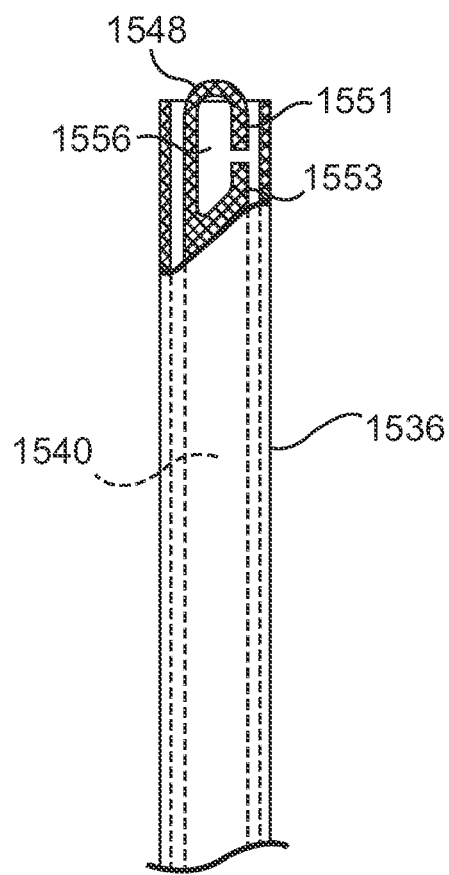
FIG. 17 shows a detailed and partially sectional view of a support member and release element in accordance with another embodiment of the invention, in an engaged state.
Figure 18:
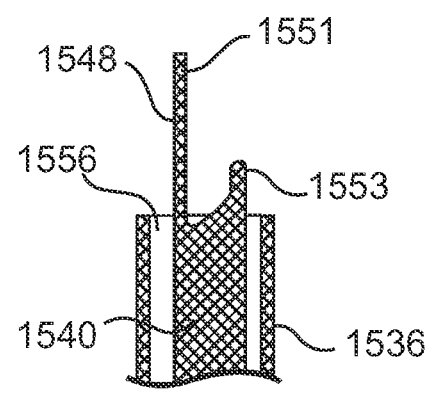
FIG. 18 shows a detailed view of a portion of the support member and release element shown in FIG. 17, in a released state.

FIGS. 17 and 18 illustrate a support member 1536 and release element 1540 according to another embodiment of the invention. The support member 1536 is a tubular structure having an opening 1556 on its distal end. The release element 1540 is an elongate member movable within the support member 1536 between retracted and extended positions. A finger on the distal end 1548 of the release element 1540 has a tang 1551 and an inner element 1553 that cooperate to provide a functional engagement portion. The distal end 1548 is formed with the tang 1551 and inner element 1553 separated and spaced from one another when the release element 1540 is in its released state shown in FIG. 18 with the distal end 1548 extending from the opening 1556 of the support member 1536. The tang 1551 is formed of flexible and resilient material, enabling the tang to be deformed from its free or native state into the hook shape of the capture position shown in FIG. 17. When release element 1540 is in the engaged state shown in FIG. 17, the tang 1551 is retained in the capture position adjacent to inner element 1553.

The tang 1551 of release element 1540 can engage a release structure such a suture loop (not shown) on a CSD (also not shown) when the release element is in the engaged state. When moved to the released state shown in FIG. 18, the tang 1551 will return to its native state to release the release structure. Locating the tang 1551 and inner element 1553 at the opening 1556 on the distal end of the support member 1536 can enhance the accuracy by which the CSD can be positioning on the patient's heart.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

The invention claimed is:

1. An apparatus including a cardiac support device (CSD) and an apparatus for placing the CSD on a heart, comprising:
   a CSD;
   a plurality of release structures including a cord on the CSD;
   a body;
   a deployment mechanism on the body for supporting the CSD in an open position for placement on the heart, the deployment mechanism including a plurality of elongate support members; and
   a release mechanism coupled to the deployment mechanism for releasably mounting the CSD to the deployment mechanism, the release mechanism including:
      a plurality of release elements coupled to the support members and movable between engaged and released states with respect to the support members, each of the release elements releasably engaged to the cord of one of the release structures on the CSD in the engaged state and disengaged from the cord of the release structures in the released state; and
      a release actuator coupled to the release elements for actuating the release elements by moving the release elements between the engaged and released states to release the CSD from the deployment mechanism.

2. The apparatus of claim 1 further comprising at least one lubricious element releasably coupled to the CSD by the release mechanism, wherein the release mechanism is operable to de-couple at least a portion of the lubricious element from the CSD.

3. The apparatus of claim 1 wherein the support members are generally tubular, and wherein the release elements are at least partially disposed within the support members.

4. The apparatus of claim 1 wherein:
   the support members include a distal portion having a first opening;
   the release structures include a flexible band disposed about and coupled to at least a portion of the CSD and extending at least partially into the first opening;
   the release elements in the engaged state extend at least partially into the first opening such that the flexible band is frictionally engaged by the support members and the release elements; and
   the release elements in the released state are retracted from the first opening to disengage the flexible band from the support members and the release elements.

5. The apparatus of claim 1 wherein:
   the release structures include a projecting member, and
   the release elements engage the projecting member for coupling the CSD to the support members.

6. The apparatus of claim 1 wherein the release elements are each slidably coupled to one of the support members.

7. The apparatus of claim 6 wherein the release mechanism further includes a plurality of release actuators each coupled to one of the release elements for individually moving the release element relative to the respective support member.

8. The apparatus of claim 7 wherein:
the release elements are elongated release members each having a proximal end; and
the release actuators each include a tab operable by a user and connected to the proximal end of a respective release member.

9. The apparatus of claim 6 wherein the release actuator moves the plurality of release elements relative to the support members.

10. The apparatus of claim 6 further comprising a first control mechanism on the body for moving the plurality of support members together with the release elements.

11. The apparatus of claim 10 further comprising a plurality of second control mechanisms on the body each for individually moving one of the support members together with the respective release element.

12. The apparatus of claim 1 wherein:
the release elements are elongated release members each having a proximal end; and
the release actuators each include a tab operable by a user and connected to the proximal end of a respective release member.

13. An apparatus for placing a cardiac support device (CSD) on a heart, the apparatus comprising:
a body;
a deployment mechanism on the body for supporting a CSD in an open position for placement on a heart, wherein the deployment mechanism includes a plurality of elongate support members;
a release mechanism coupled to the deployment mechanism for releasably mounting a CSD to the deployment mechanism, the release mechanism including:
a plurality of release elements for releasably engaging a CSD, each slidably coupled to one of the support members, wherein the release elements are elongated release members each having a proximal end; and
a plurality of release actuators, each coupled to one of the release elements to individually move the release elements relative to the respective support member and release a CSD, and wherein the release actuators each include a tab operable by a user and connected to a proximal end of a respective release member.

14. The apparatus of claim 13 and further comprising a CSD having release structures, wherein each of the release structures is releasably engaged by a release element of the release mechanism.

15. The apparatus of claim 14 wherein the release structures comprise loops.

16. The apparatus of claim 13 wherein the release elements are at least partially disposed within the support members.

17. The apparatus of claim 13 wherein the release actuator moves the plurality of release elements relative to the support members.

18. An apparatus for placing a cardiac support device (CSD) on a heart, the apparatus comprising:
a body;
a deployment mechanism on the body for supporting a CSD in an open position for placement on a heart, wherein the deployment mechanism includes a plurality of elongate support members;
a release mechanism coupled to the deployment mechanism for releasably mounting a CSD to the deployment mechanism, the release mechanism including:
a plurality of release elements for releasably engaging a CSD, each slidably coupled to one of the support members; and
a release actuator coupled to the release elements to actuate the release elements and release a CSD; and
a first control mechanism on the body for moving the plurality of support members together with the release elements.

19. The apparatus of claim 18 further comprising a plurality of second control mechanisms on the body each for individually moving one of the support members together with the respective release element.

* * * * *

UNITED STATES PATENT AND TRADEMARK OFFICE
CERTIFICATE OF CORRECTION

PATENT NO. : 7,651,462 B2
APPLICATION NO. : 11/487953
DATED : January 26, 2010
INVENTOR(S) : Hjelle et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 460 days.

Signed and Sealed this

Twenty-eighth Day of December, 2010

David J. Kappos
*Director of the United States Patent and Trademark Office*